United States Patent [19]

Spielberg

[11] Patent Number: 5,045,063
[45] Date of Patent: Sep. 3, 1991

[54] HYPODERMIC SYRINGE

[76] Inventor: Alissa R. Spielberg, 10 Pinewood Cir., Wellesley, Mass. 02181

[21] Appl. No.: 358,886

[22] Filed: May 30, 1989

[51] Int. Cl.5 .............................................. A61M 5/00
[52] U.S. Cl. .................................... 604/110; 604/218; 604/220
[58] Field of Search ............... 604/110, 187, 218, 228, 604/221, 222

[56] References Cited

U.S. PATENT DOCUMENTS

| | | | |
|---|---|---|---|
| 4,233,975 | 11/1980 | Yerman | 604/110 X |
| 4,391,272 | 7/1983 | Staempfli | 604/110 |
| 4,863,427 | 9/1989 | Cocchi | 604/110 |
| 4,941,879 | 7/1990 | Butler et al. | 604/110 |

Primary Examiner—John D. Yasko
Attorney, Agent, or Firm—Cesari and McKenna

[57] ABSTRACT

A non-reusable hypodermic syringe is disclosed having a body having a barrel for receiving fluid to be injected including an aperture in the body at the forward end of the syringe, a plunger carrying a piston having a collar thereon and of larger size than the aperture, the collar deformable in a first direction for passage through the aperture and resisting deformation in a second direction for blocking passage through the aperture.

2 Claims, 2 Drawing Sheets

0
HYPODERMIC SYRINGE

BACKGROUND OF THE INVENTION

A. Field Of The Invention

The invention relates to hypodermic syringes, and comprises a syringe whose utilization is restricted to a single use.

B. Prior Art

Hypodermic syringes which inject fluid substances into the body traditionally have allowed for repeated use of the syringe. This feature was not only acceptable, but also necessary, when syringes were more expensive and when their distribution and use was restricted to professional personnel who followed established sterilization protocols before re-use.

At present, however, with syringe re-use widespread among non-medical personnel, such a capability for repeated use has become a liability rather than an asset. Contaminants from the prior use remain within the barrel and, if not removed by sterilization, can pose a significant threat to subsequent users. Accordingly, a syringe capable of re-use is now unacceptable in uncontrolled environments (that is, outside a hospital setting). Such re-use has been a significant factor in spreading the AIDS virus, hepatitis, and other infections among drug users.

SUMMARY OF THE INVENTION

A. Objects Of The Invention

Accordingly, it is an object of the invention to provide an improved hypodermic syringe.

Further, it is an object of the invention to provide a hypodermic syringe which can be used for only a single injection.

Still a further object of the invention is to provide a hypodermic syringe which is capable of only a single use and is simple and inexpensive to manufacture.

B. Brief Summary Of The Invention

In accordance with a preferred embodiment of my invention, a hypodermic syringe capable of but a single use is formed from an outer body or barrel, preferably of generally cylindrical shape, and an internal plunger movable within the body for pressurizing the fluid to be injected. The body has a preferably asymmetric shaped aperture formed therein for coaction with a restrictor element on the plunger.

The restrictor and its corresponding aperture are so located relative to each other that the plunger may be withdrawn freely on initial use of the syringe, to enable filling the syringe. However, during use of the syringe, as the plunger is pushed further into the barrel to pressurize the fluid within the barrel and thus inject it into a body, the restrictor is deformed as it passes through the aperture. After clearing the aperture, the restrictor returns approximately to its undeformed position in which it is unable to pass backwardly through the aperture. Accordingly, the syringe is disabled for re-use.

DETAILED DESCRIPTION OF THE INVENTION

The foregoing and other and further objects and features of the invention will more readily be understood on reference to the following detailed description of the invention, when taken in connection with the accompanying drawings in which.

Figure 1:
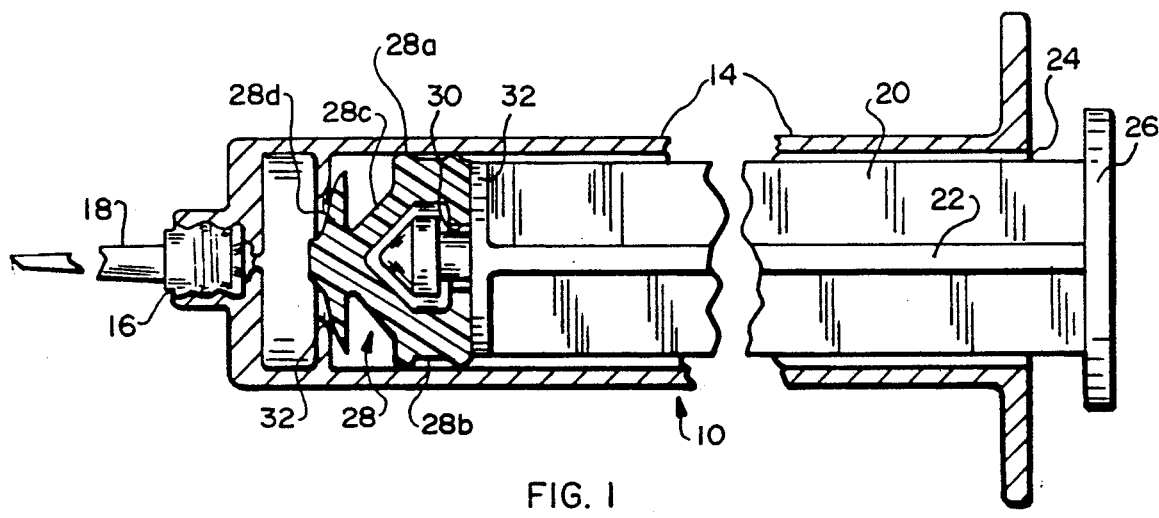
FIG. 1 is a cross-sectional view of a hypodermic syringe constructed in accordance with the present invention and showing the restrictor portion of the syringe just before its entry into the restricting aperture of the barrel.

Referring now particularly to FIG. 1, a hypodermic syringe 10 in accordance with the present invention has a body of generally conventional shape and comprises a barrel 14 terminating at one end in a nozzle 16 for receiving a needle 18 which is to pierce the skin of a body and thereby enable injection of the contents of the syringe. A plunger 20 having a shaft 22 of cruciform shape extends through an open end 24 of the barrel 14. The plunger terminates at one end in a thumb rest 26 and carries, at the other end, a piston 28 having an aperture 30 in a rear face thereof. A cylindrical head 22a of shaft 22 of diameter larger than aperture 30 extends through the aperture for mounting the piston on the shaft. A circular plate 32 fixed to the shaft provides a large flat surface for pushing against the rear wall of the piston when liquid is to be discharged from the syringe.

In accordance with the present invention, the piston 28 comprises a generally cylindrical segment 28a having a circumferentially formed groove 28b therein. The piston has a tapering front face 28c which meets with a collar 28d extending from the front surface. The piston is preferably formed from a resilient material such as rubber which forms a seal with the side wall of the syringe and which allows at least limited deformation of the collar 28d. The syringe is filled with fluid in the conventional manner by withdrawing the thumb rest 26 from the body 12 while immersing the needle 18 in the fluid to be injected.

Figure 2A:
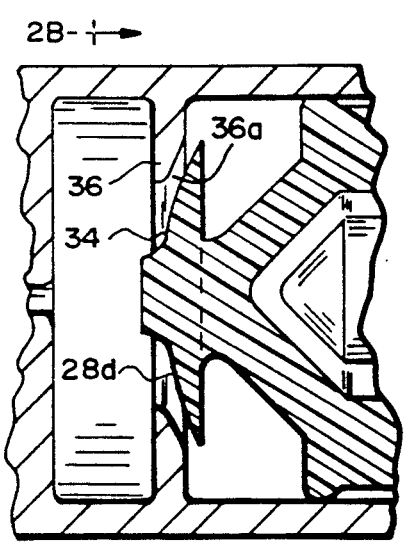
FIG. 2A is an enlarged cross-sectional view of the restrictor portion of the syringe of FIG. 1.
Figure 2B:
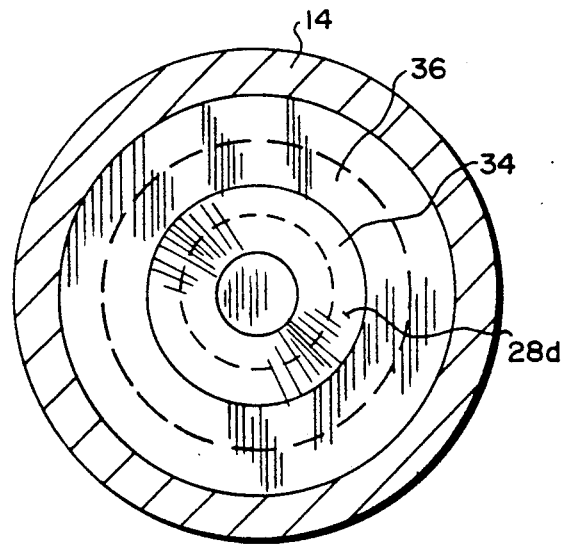
FIG. 2B is an enlarged transverse sectional view of the syringe of FIG. 1 in the direction 2B—2B of FIG. 1.

Referring now to FIG. 2 as well as FIG. 1, an asymmetric restricting aperture is formed within the barrel 14 by a circular plate 36 which preferably has a forwardly tapering face 36a forming an aperture 34 of cross section less than the diameter of collar 28d. The collar 28d is formed of a material such as polypropylene which has significant strength but which also has a relatively high degree of resilience. The latter property, in combination with the shape of the collar, enables the collar to deform sufficiently in the rearward direction to enable the collar to pass through the aperture 34 in plate 36 when the plunger is moved inwardly of the barrel to inject the fluid. However, this resilience also enables the collar to return generally to its initial state after passage through the aperture. In this state, the collar, because of its shape, and because of the diminished size of the aperture, presented to movement in the rearward direction, is blocked from passage through the aperture in the rearward direction. To further facilitate passage of the collar through the aperture, the rear face 28d of the collar may be curved inwardly from a point slightly inward of its rim to the point of attachment to the shaft in order to facilitate deformation of the collar as it passes through the plate 36.

Figure 3:
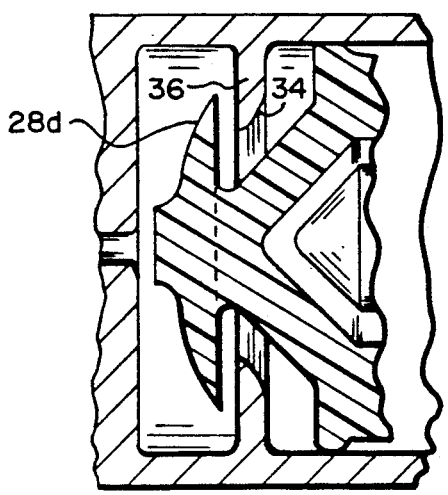
FIG. 3 is a cross-sectional view of the syringe of FIG. 1 showing the restrictor just after its passage through the restricting aperture of the barrel.

As provided to the initial user, the plunger 20 is slightly withdrawn from the barrel 14 so that the collar 28d lies to the rear of the plate 36. In this condition, the plunger can be withdrawn while the tip of the needle is inserted in a liquid to be injected, to thereby enable filling of the syringe. Thereafter, the plunger is pressed forward in the usual manner in order to inject the liquid. As the user presses inwardly on the thumb plate and forces the piston down the barrel to the point where the collar 28d penetrates the aperture 34, the collar initially deforms as it passes through the aperture, and then resumes its initial shape on clearing the aperture, as shown in FIG. 3. The shape of the collar 28d, as well as the aperture 34, thereafter prevent withdrawal of the collar through the aperture in the rearward direction, thus disabling the syringe from further use. To this end, the size of the aperture 32 is preferably also so proportioned in relation to the resiliency of the material of the piston that when a rearward force is applied to the plunger 20 the head 22a is pulled from the piston before the collar 28d can be withdrawn through the aperture 34.

Figure 4:
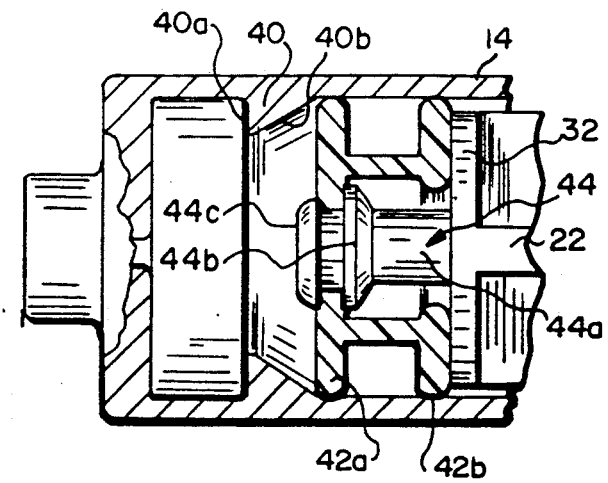
FIGS. 4 and 4A are cross-sectional views of an alternative form of restrictor in accordance with the present invention in which the restrictor aperture is formed by an internal rim on the side wall of the syringe, and showing the restrictor just before (FIG. 4) and after (FIG. 4A) its passage through the restricting aperture.

Turning now to FIG. 4, an alternative form of restrictor plate is shown. In FIG. 4, the restrictor plate is formed by an internal collar 40 on the side wall of the barrel 14 to thereby provide a generally vertical face 40a on the front (needle end) of the collar, and a rearwardly sloping face 40b on the back end thereof. The piston 42 is formed from a generally cylindrical hollow plug having lips 42a and 42b defining an annular groove 42c extending around the periphery thereof. An aperture 42d is formed in the front face of the piston and an aperture 42e is formed in the rear face thereof. A head 44 extending from piston plate 32 extends through aperture 42e in the rear face of piston 42 and has a shaft 44a carrying spaced-apart flanges 44b and 44c, respectively. Flange 44c is extended through the aperture 42d of piston 42 so as to encompass the front face of piston 42 between the flanges. Flange 44c is smaller than flange 44b so that less force is required to unseat the piston from the head 44 when the plunger is moved rearwardly than when moved forewardly.

Figure 4A:
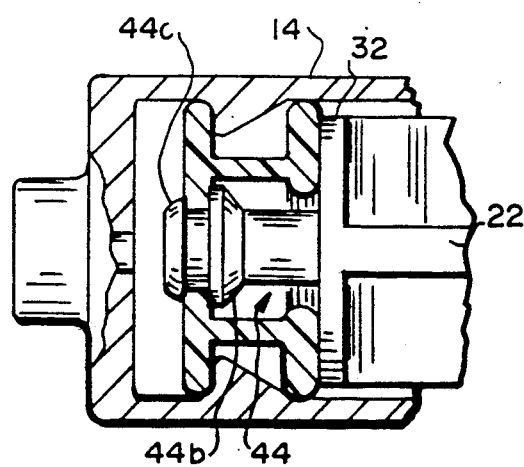

Piston 42 is formed of a resilient material such as rubber or the like, such that lips 42b and 42c resiliently press against the inner wall of barrel 14 to seal the interior as the plunger is moved within the tarrel. As received for its original use, the piston 28 lies just to the left of the collar as shown in FIG. 4. The piston is drawn backwardly for filling. When the piston is thereafter moved forward to inject the contents of the syringe, the forward lip 42b is distorted and compressed as it moves down the face 40b of the collar 40, until it reaches the front face 40a. At this point, it thereafter de-compresses and resiliently returns to its original shape, thus locking the piston from withdrawal as shown in FIG. 4A. Should withdrawal of the piston be attempted after the piston has reached the position shown in FIG. 4A, the extra resistance provided by the force of lip 42b against face 40a of collar 40 will cause flange 44c to pop through aperture 42d and thus separate plunger 22 from the piston. Accordingly, the piston will remain locked within the barrel, thereby disabling it from use.

Figure 5A:
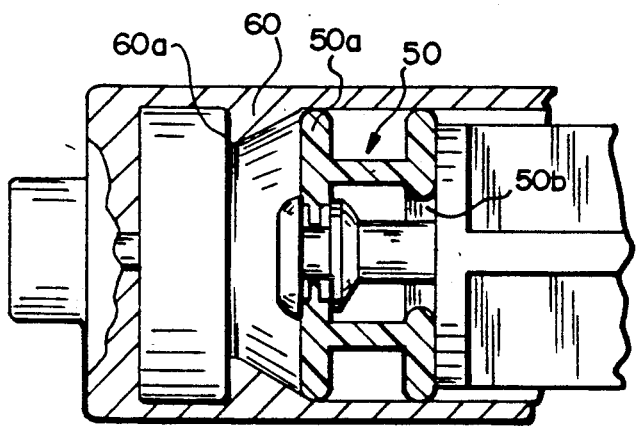
FIGS. 5A and 5B are cross-sectional views of yet another alternative form of restrictor in accordance with the present invention in which the prevention of multiple use of the syringe is further ensured by weakening a wall of the piston (FIG. 5A) or of the plunger (FIG. 5B).
Figure 5B:
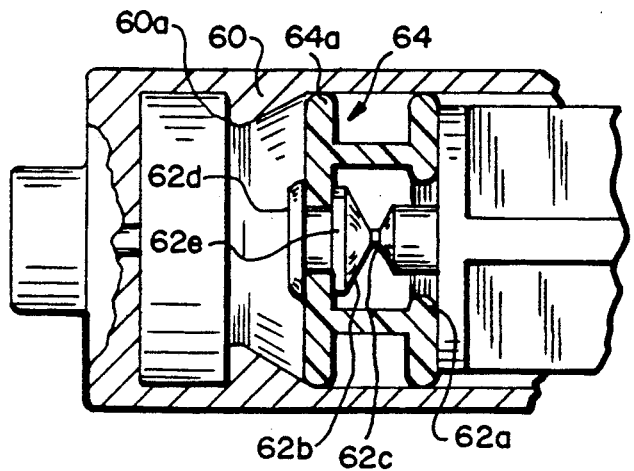

FIGS. 5A and 5B show still further alternative embodiments of the present invention. In both of these, the internal collar 40 is used in combination with a modified piston or plunger to disable the piston or the plunger from subsequent reuse.

In particular, in FIG. 5A, the piston 50 is similar to piston 42 of FIG. 4 but has a weakened wall section 52a in the front face thereof. This may be achieved, for example, by forming the front face of the piston with a thinned section in the center adjacent the plunger flanges. The weakened section need only be sufficiently strong to bear the fluid pressure arising from movement of the plunger forewardly to discharge the fluid within the syringe. The frictional forces (which are generated by the sealing resistance between the piston and the inner wall of the barrel) that act on the piston during this forward motion are borne largely by the plate 31, and not by the weakened portion of the piston. However, when the piston is moved in the rearward direction for filling, the frictional forces are borne largely by the weakened portion. This portion must therefore be sufficiently strong as to withstand the normal force caused by withdrawal of the plunger for the initial filling.

When the syringe has been used, and the front of the piston advanced to the point where its front lip 50a rests against the face 60a of collar 60, a further and substantial resistance to withdrawal is created. The force of this resistance must be borne largely by the weakened portion and, when added to the force generated by frictional resistance during rearward movement of the piston, causes the piston to rupture and thereby create a direct fluid path through the piston via the ruptured section in the front face and the aperture 50b in the rear face. When this occurs, the syringe is thereafter unusable, since the piston is no longer capable of providing the requisite fluid seal for discharge of liquid from the syringe.

In FIG. 5B, the head 62 which carries the piston 64 is formed from first and second shaft portions 62a and 62b and intermediate bridging portion 62c. As before, flanges 62d and 62e secure the piston 64. The dimensions of section 62c are such that it is able to withstand the frictional force caused by withdrawal of the plunger during normal filling operations when the piston lies to the right of collar 60, but is unable to withstand the additional force exerted on it when lip 64a has passed through the collar 60. Accordingly, only a single use is allowed by the syringe.

It will be understood that various changes may be made in the foregoing without departing from either the spirit or the scope of the invention. For example, rather than molding a collar in the interior of the barrel 14 in order to form an aperture of restricted size, the collar 60 of FIGS. 4 and 5 may be formed simply by invaginating the walls of the barrel 14 at the forward end. This serves to restrict the cross section of the syringe at the desired location, while simplifying the forming operation for the syringe. Other changes of similar character will occur to those skilled in the art without modifying the spirit of the invention, and it is intended that such changes be understood as being encompassed herein.

CONCLUSION

From the foregoing, it will be seen that I have provided an improved hypodermic syringe, in particular, one that precludes re-use after its initial use. This restriction can be an effective instrument in helping to prevent the spread of infection caused by syringe re-use. Various embodiments have been shown for ensuring this limited use, and it will be understood that other modifications may be made to the invention described herein without departing from either its spirit or its scope.

Having illustrated and described my invention, I claim:

1. A non-reusable hypodermic syringe comprising:
   A a body having a barrel for receiving a fluid to be injected;
   B means forming an asymmetric aperture in said body and having a face tapering toward the forward end of said syringe;
   C a plunger carrying a piston for ejecting fluid from said body;
   D a collar on said piston, said collar:
      (1) of larger size than said aperture,
      (2) of smaller size than said barrel,
      (3) deformable in a first direction for enabling passage through said aperture in said first direction, and
      (4) resisting deformation in a second direction for blocking passage through said aperture in said second direction.

2. A hypodermic syringe according to claim 1 in which said piston collar has a rearwardly sloping face on the front thereof, and a concave face on the rear thereof, to facilitate deformation in a rearward direction, and resist deformation in a forward direction.

* * * * *